United States Patent [19]

Zalewski et al.

[11] 4,402,606

[45] Sep. 6, 1983

[54] OPTOGALVANIC INTRACAVITY QUANTITATIVE DETECTOR AND METHOD FOR ITS USE

[75] Inventors: Edward F. Zalewski, Gaithersburg, Md.; Richard A. Keller; Charles T. Apel, both of Los Alamos, N. Mex.,

[73] Assignee: The United States of America as represented by the U.S. Department of Energy, Washington, D.C.

[21] Appl. No.: 238,236

[22] Filed: Feb. 25, 1981

[51] Int. Cl.³ .......................... G01J 3/30; G01N 21/72
[52] U.S. Cl. .................................... 356/315; 356/318; 324/65 R
[58] Field of Search ...................... 356/318, 315, 313; 250/343, 423 P; 324/65 R

[56] References Cited

U.S. PATENT DOCUMENTS 4,148,586  5/1979  Green et al. ........................ 356/318
4,184,127  1/1980  Green et al. ........................ 331/94.5

OTHER PUBLICATIONS

Konjevic et al., "Dye-Laser for Absorption Trace Analysis of Sodium", Spectroscopy Letters, vol. 6, #3, 1973, pp. 177-181.

Maeda et al., "Dye-Laser Amplified, Atomic Abs. Flame Spectroscopy", Optics Communication, vol. 13, #3, 1975, pp. 314-317.

Primary Examiner—F. L. Evans
Assistant Examiner—L. A. Dietert
Attorney, Agent, or Firm—Paul D. Gaetjens; Robert W. Weig; Richard G. Besha

[57] ABSTRACT

The disclosure relates to an optogalvanic intracavity detector and method for its use. Measurement is made of the amount of light absorbed by atoms, small molecules and ions in a laser cavity utilizing laser-produced changes in plasmas containing the same atoms, molecules, or ions.

8 Claims, 6 Drawing Figures

OPTOGALVANIC INTRACAVITY QUANTITATIVE DETECTOR AND METHOD FOR ITS USE

BACKGROUND OF THE INVENTION

The invention relates to detection and measurement of the amount of light absorbed by atoms, small molecules and ions in a laser cavity via laser-produced changes in plasmas containing the same atoms, small molecules, or ions. It is a result of a contract with the Department of Energy (Contract W-7405-ENG-36).

Spectroscopic detection of elements is traditionally based on light dispersion techniques. Typically, the atoms of a sample are excited in an arc or other device, the emitted light being passed through a spectroscopic system and dispersed into the characteristic wavelengths of the various elements. Quantitative and qualitative elemental determination can be performed either photographically or electronically by measuring the position and intensity of the characteristic spectrum for any given element. Photographic techniques date from the 1870's; photomultiplier tube electronic techniques date from the 1940's.

The advent of the tunable laser spurred research with the optogalvanic effect (OGE) in which a laser induced transition at a given wavelength modified the current drawn by a laser-irradiated hollow cathode discharge. As illustrated by U.S. Pat. Nos. 4,148,127 and 4,148,586 to Green et al.; studies of OGE have lead to some very sensitive detection apparatus and methods being established for certain elements.

It is known that optogalvanic signals can be induced by irradiation of discharges using discharge tubes, plasma arcs, and the like. However the application of OGE in a nondispersive, specific element detector such as with the present invention has not been demonstrated or suggested.

High resolution, such as 2 parts in $10^6$, spectrographs and interferometers have been utilized but, as is well known to those skilled in the art, the apparatus necessary to practice such methods are cumbersome and expensive.

It is therefore an object of the present invention to provide quantitative detection of atoms, small molecules and ions with the precision of a few parts per billion (ppb) or better.

It is another object of the invention to greatly reduce the cost of quantitative detection.

It is yet another object of the invention to greatly increase the sensitivity of quantitative spectral detection.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularily pointed out in the appended claims.

In accordance with the present invention there is provided an apparatus and method for determining quantitatively the amount of a selected species, such as an element, molecule or ion in a substance. The substance is disposed within a laser cavity positioned to receive the beam of the laser. For example, a plasma may be produced within the laser cavity by means of an analytical flame. A hollow cathode, positive column discharge or other flame with electrical probes it is positioned to receive the laser's beam and a voltage responsive means for determining a change in voltage across the hollow cathode or other device responsive to the optogalvanic effect provides a voltage indicative of the amount of the selected element, molecule or ion in the substance within the laser cavity. A beam chopper is preferably used in order to produce an ac signal for analysis.

One advantage of the instant invention is that it is very inexpensive to practice in comparison with prior art spectrographic techniques.

Another advantage of the instant invention is that it yields very high sensitivity, to less than about a few parts per billion.

BRIEF DESCRIPTION OF THE DRAWINGS

The accompanying drawings which are incorporated and form a part of the specification, illustrate a preferred embodiment of the present invention and together with the description serve to explain the principles of the invention. In the drawings.

DETAILED DESCRIPTION OF A PREFERRED EMBODIMENT OF THE INVENTION

Figure 1:
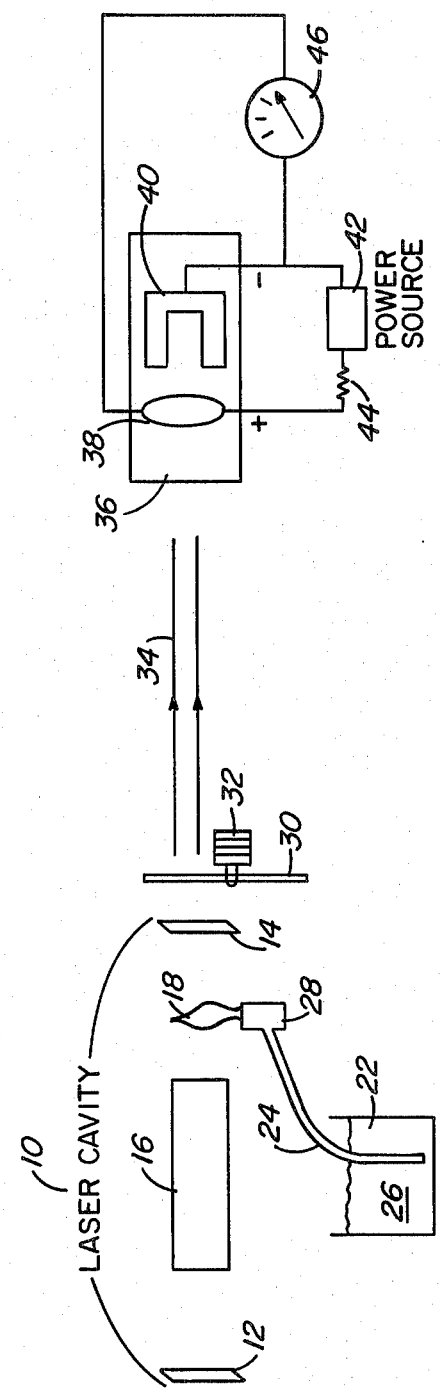
FIG. 1 illustrates a preferred embodiment of the invention.

Reference is now made to FIG. 1 which shows a laser cavity 10 comprising a pair of mirrors 12 and 14 and laser gain medium 16. Disposed within laser cavity 10 is a flame 18 produced by a burner 28 connected to a container 22 by a conduit 24. Within container 22 is the substance or mixture 26 it is desired to quantitatively analyze for the presence of one or more elements. Those skilled in the art will recognize other sample introduction systems (cells, plasma discharges, etc.) would permit the study of the speciation of the substance—molecules, atoms, ions. Although a liquid is shown being burned by flame 18, it will be appreciated by those skilled in the art that a solid, powder, or gas sample could be introduced and atomized. Analytical flame burning techniques are very well known. The liquid atomization technique illustrated is representative of all analytical flame techniques. A chopper 30 driven by a motor 32 is provided to synchronize a laser beam 34 with the electronics associated with the detector. Beam 34 exits the laser and impinges on a detector 36 comprising, for example, a circular anode 38 and a hollow cathode 40. The detector 36 is electrically connected to a power source 42 through a load resistor 44. The electrical impedance of detector 36 can be monitored by a voltage sensitive instrument such as a voltmeter 46, lock-in amplifier, or ammeter. Those skilled in the art will appreciate that the particular detector used should be specifically designed for the atom, small molecule, ion or the like to be detected and that other devices may be used as detector 36. Examples are positive column discharge and second analytical flames.

In an experiment solutions of NaCl were prepared utilizing deionized water. Precautions were taken to avoid sodium contamination. These solutions were aspirated at 1.3 cm$^3$ min$^{-1}$ into a Beckman Model 4020 hydrogen torch which was disposed inside the cavity of a Coherent model 590 cw dye laser. The wavelength selective element was a single plate Lyot filter. In order to accommodate the flame the laser cavity was extended about 25 cm, the length of the flame in the laser path being approximately 1 cm. The laser wavelength was tuned to overlap one of the sodium resonance lines (589.0 mm) and the output was directed through a chopper operated at 170 Hz into a commercial sodium hollow cathode lamp.

Optogalvanic signals were detected by measuring the voltage across the lamp with a lock-in amplifier syncronized to the chopper, the output of the lock-in amplifier being integrated for 10 seconds with a voltage-to-frequency converter and a counter.

The dye laser spectrum was measured with a one meter scanning monochromator 5 $\mu$m slits. The output laser power was approximately 5 mW spread over a bandwidth of about 0.4 nm, and the circulating power inside the cavity was well above threshold.

Figure 3:
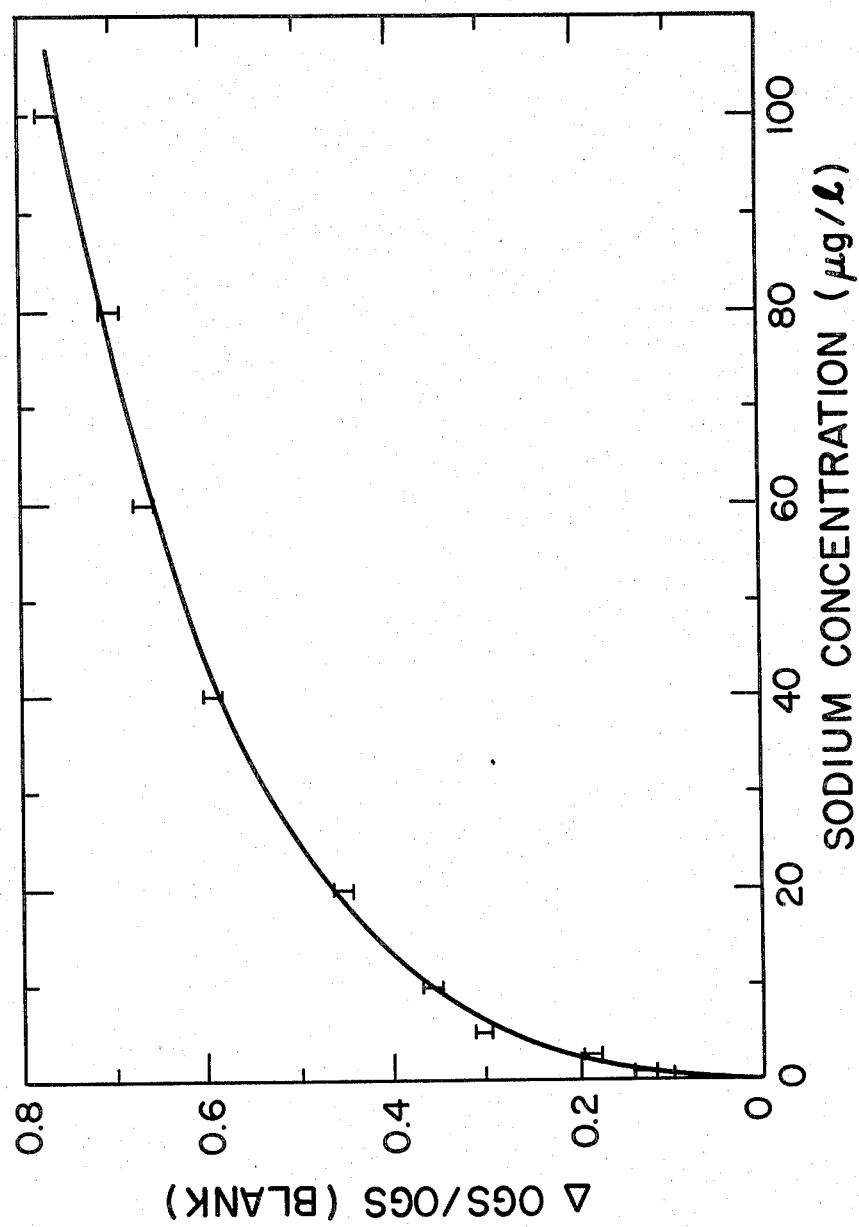
Figure 4:
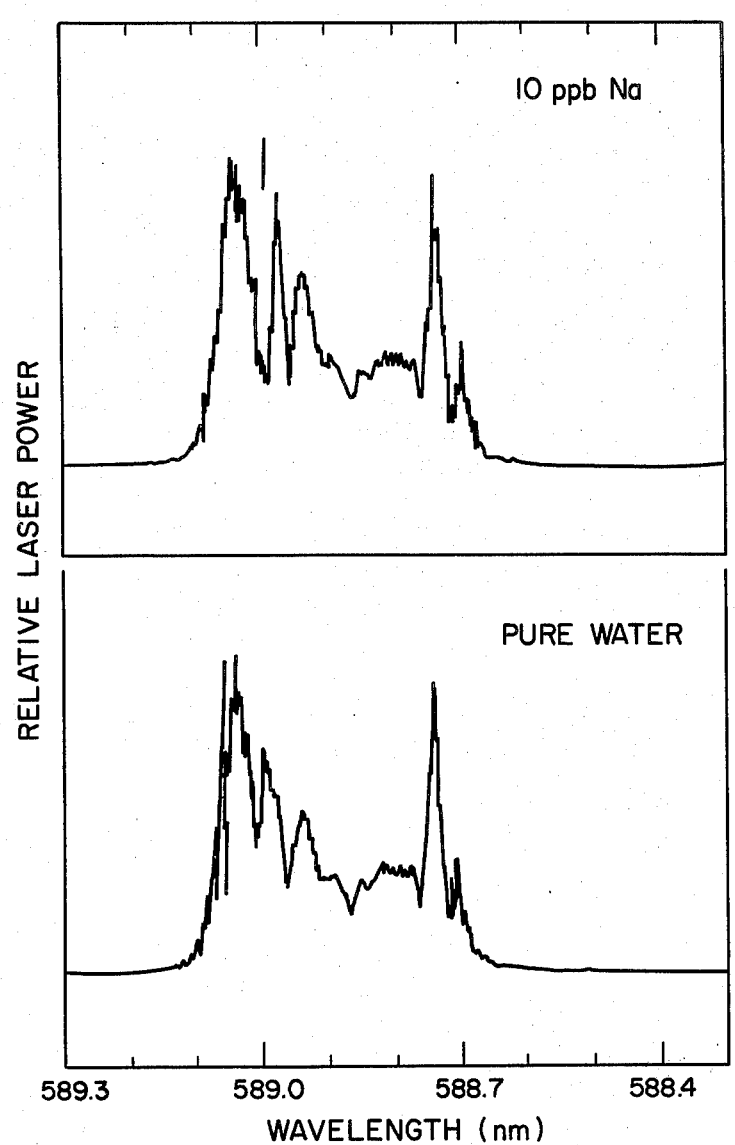

Sodium solutions at concentrations ranging from 1 82 g/l to 100 $\mu$g/l (1–100 ppb of Na) and a blank of the deionized water was aspirated into the flame and the optogalvanic signals (OGS) measured. FIG. 3 is a plot of the relative change in the OGS, the difference between the OGS for each Na sample and the blank divided by the OGS of the blank, versus the sodium concentration. The standard deviation of three readings of the OGS was generally less than 2% but increased to 10% at the 1 ppb level. Continuation of the measurements to lower concentrations was not precluded by poor signal to noise ratio but instead by the difficulty in preparing uncontaminated sodium solutions at such levels. Even though no attempt was made to maximize the intracavity enhancement for the study, the detection limit in practicing the invention appears to be well below 1 $\mu$g/l. Those skilled in the art will recognize that this sensitivity is significant, particularly in view of the relative low cost of the apparatus of the invention. In a comparison of OG detection with spectroscopic detection, scanning monochromator measurements of the cw dye laser spectrum are shown in FIG. 4 for a 10 $\mu$g/l Na solution and pure water aspirated into the flame. When compared to the intracavity absorption spectrum of pure water, the spectrum of the Na solution shows an absorption in the region of the 589 nm Na resonance line with a compensating increase in laser emission and shorter wavelengths. From the noise in the spectra it is apparent that an attempt to quantify the amount of radiation absorbed by the Na at this level would be imprecise. Furthermore, the effect may not be discernable at much lower Na concentration with this spectrograph. This contrasts to OG detection in accordance with the invention wherein the precision of the blank and 10 $\mu$g/l Na solutions were 1.0 and 1.5%, respectively.

Figure 5:
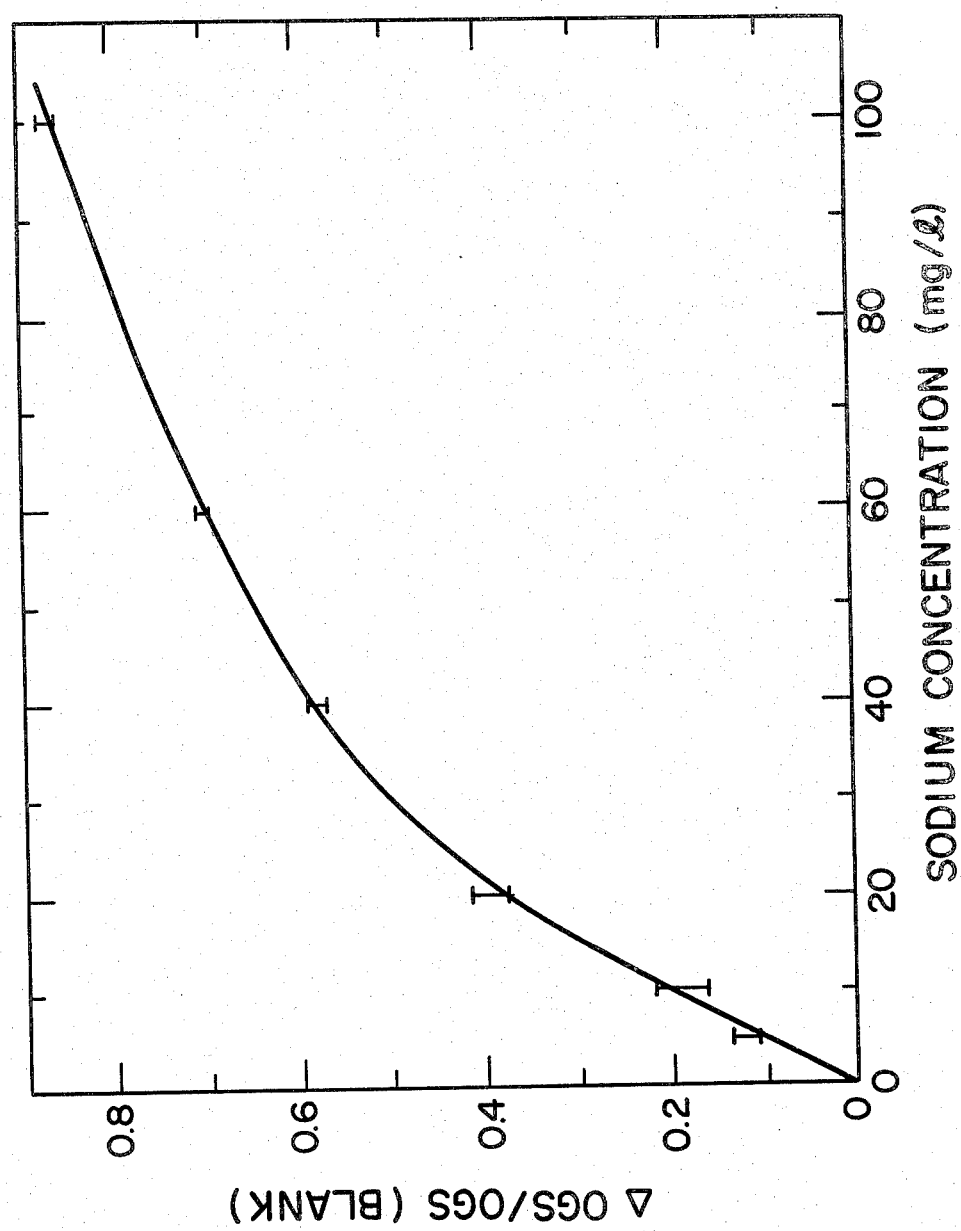
Figure 6:
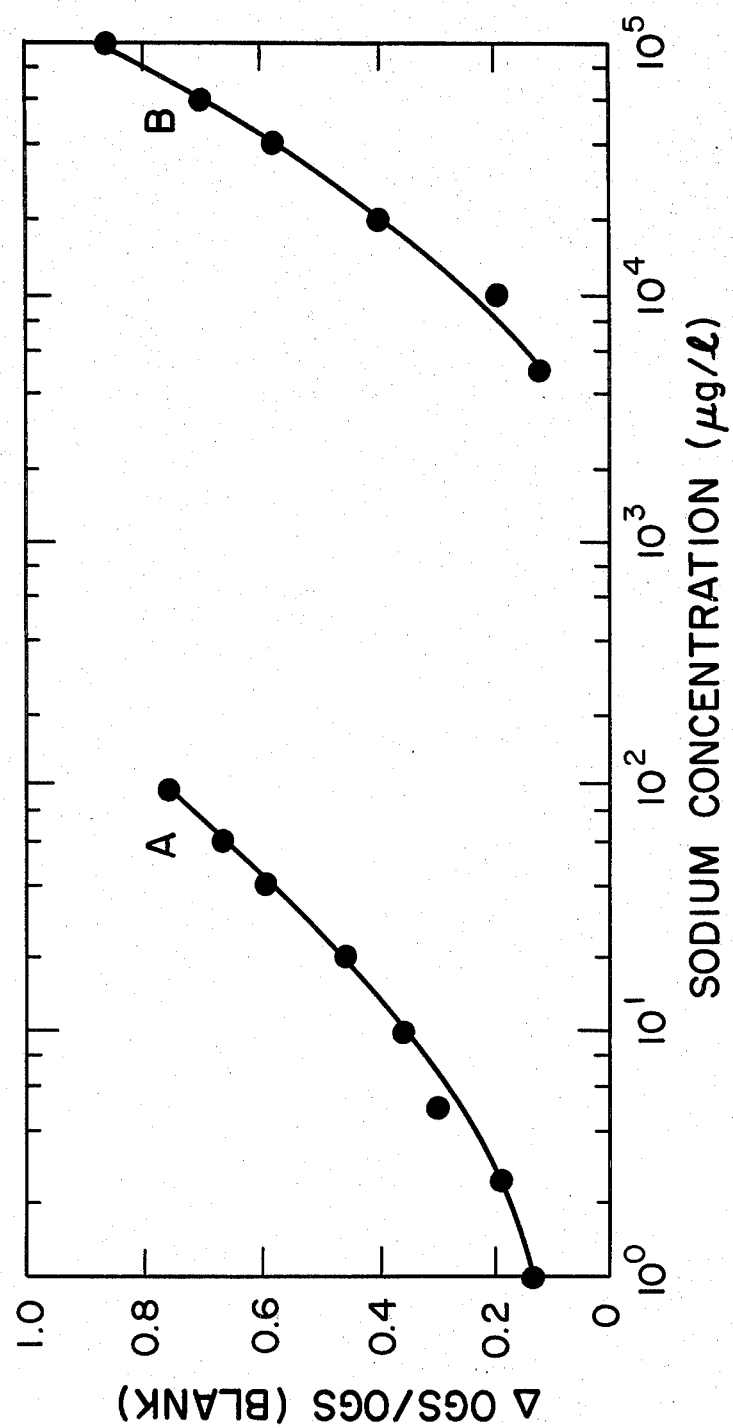

Another experiment was carried out with the samples disposed outside the laser cavity. The range of Na concentrations used in measurements was from 5 mg/l to 100 mg/l. The results are shown in FIG. 5. The Na detection limit appears to be on the order of 1 mg/l. FIG. 6 illustrates a comparison of the OG detection of the extracavity (A) and intracavity (B) absorption measurements of Na in a flame. The enhancement sensitivity realized by placing the flame inside the cavity is about four thousand. Those skilled in the art will appreciate that considerable improvement could be realized because enhancements as high as $10^5$ have been achieved when the laser was operated close to threshold.

As can be seen, OG detection in accordance with the present invention is a very promising alternative to expensive high resolution spectrography for intracavity absorption measurements. OG detection in practicing the invention is specific, sensitive, simple to use and relatively inexpensive. The feasibility measurement indicated by experiment indicates a detection limit of less than 1 $\mu$g/l for Na. Those skilled in the art will recognize that an increase in sensitivity by a factor of 10 to 100 should be easily achieved by simple improvements. For example, the length of the flame in the cavity could be increased and the laser could be operated closer to threshold.

Figure 2:
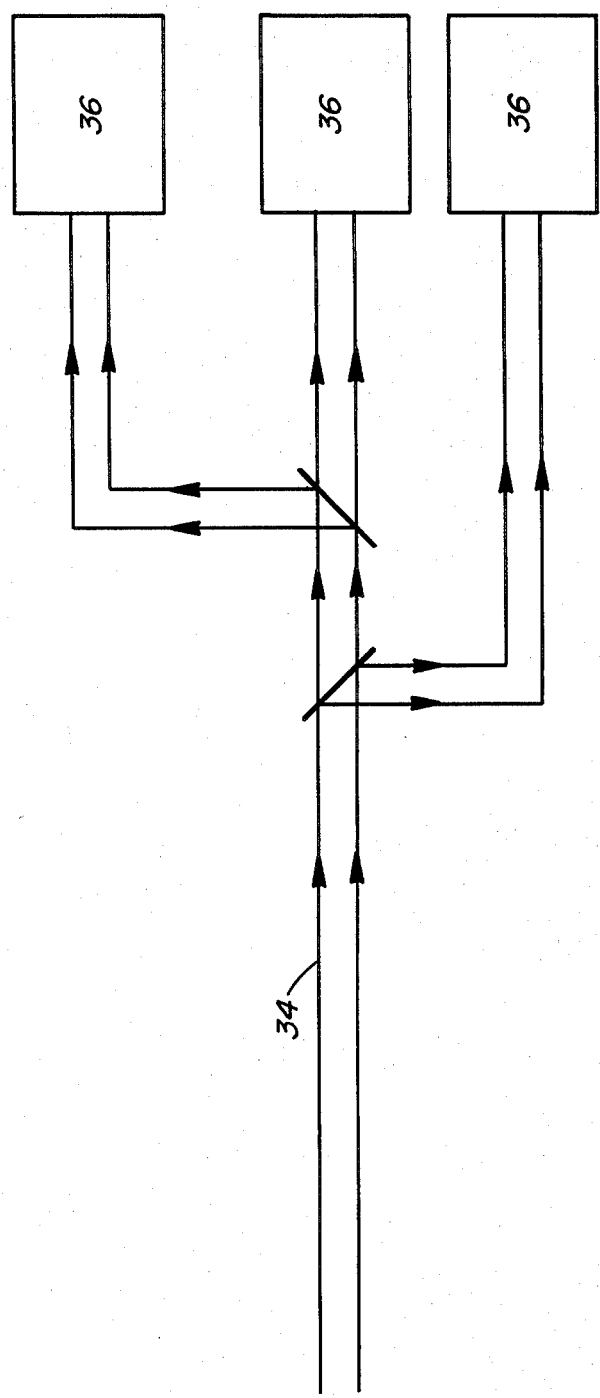
FIG. 2 shows a plurality of detectors usable with the FIG. 1 embodiment.

Optogalvanic detection of intracavity absorption is readily applicable to many elements other than sodium. Multi-element analysis can be accomplished by sweeping the laser wavelength or using a very broadband laser and having several hollow cathode detectors as seen in FIG. 2, each selective for a specific element. In addition, OG detection is not restricted to cw dye lasers but is practicable with a variety of lasers including pulsed lasers. OG detection of intracavity absorption can also be extended to sub-Doppler width detection and isotopic analysis by utilizing intermodulation spectroscopy. Such applications are, of course, beyond the resolution limits of conventional spectroscopy.

The foregoing description of a preferred embodiment of the invention has been presented for purposes of illustration and description and is not intended to be exhaustive or to limit the invention to the precise form disclosed. It was chosen and described in order to best explain the principles of the invention and their practical application to thereby enable others skilled in the art to best utilize the invention in various embodiments and with various modifications as are suited to the particular use contemplated. It is intended that the scope of the invention be defined by the claims appended hereto.

What is claimed is:

1. An apparatus for quantitatively determining the amount of a species selected from the group consisting of ions, molecules, and atoms contained in a first substance comprising at least said species, said apparatus comprising in combination:
   a. means for producing laser radiation at wavelengths which can be absorbed by at least a portion of said species;
   b. means for producing an electrical discharge in a second substance whereby the product of said electrical discharge includes at least said species, whereby said species takes part in said electrical discharge, and whereby said laser radiation interacts with at least a portion of said species appearing in said electrical discharge thereby producing an optogalvanic effect therein;
   c. means for observing said optogalvanic effect in said portion of said species in said electrical discharge which interacts with said laser radiation; and
   d. means for causing at least a portion of said first substance to interact with said laser radiation at a location spaced between said laser radiation producing means and said optogalvanic observing means thereby permitting said portion of said species to absorb a quantity of said laser radiation, whereby absorption of said quantity of said laser radiation by said portion of said species causes a change in said observed optogalvanic effect in said portion of said electrical discharge which interacts with said laser radiation.

2. The apparatus as described in claim 1, wherein said electrical discharge producing means includes a hollow cathode and an anode, said hollow cathode to be used to hold said second substance.

3. The apparatus as described in claim 2, and including also means for intermittently interrupting said laser radiation before it enters said first substance in order to create an ac signal output from said optogalvanic effect observing means.

4. The apparatus as described in claim 3, wherein means are provided for recording said observed ac signal output from said optogalvanic effect observing means.

5. The apparatus as described in claim 4, wherein said laser radiation producing means includes a laser cavity and wherein said means for causing said portion of said first substance to interact with said laser radiation is located within said laser cavity thereby increasing said change in said observed optogalvanic effect in said portion of said electrical discharge which interacts with said laser radiation above a level attainable when said means for causing said portion of said first substance to interact with said laser radiation is located outside of said laser cavity.

6. The apparatus as described in claim 5, wherein said optogalvanic effect observing means includes voltage responsive means for determining voltages appearing between said hollow cathode and said anode.

7. The apparatus as described in claim 6, wherein said means for causing said portion of said first substance to interact with said laser radiation includes a flame which quantitatively causes said portion of said species to interact with said laser radiation.

8. A method for quantitatively determining the amount of a species selected from the group consisting of ions, molecules and atoms contained in a first substance which comprises at least said species, said method comprising the steps of:

a. producing laser radiation at wavelengths which can be absorbed by at least a portion of said species;

b. producing an electrical discharge in a second substance, the product of said electrical discharge including at least said species, said species taking part in said electrical discharge and said laser radiation interacting with at least a portion of said species appearing in said electrical discharge to produce an optogalvanic effect therein;

c. observing said optogalvanic effect in said portion of said species in said electrical discharge which interacts with said laser radiation; and d. causing at least a portion of said first substance to interact with said laser radiation providing for said portion of said species to absorb a quantity of said laser radiation, said absorption of said quantity of said laser radiation by said portion of said species causing a change in said observed optogalvanic effect in said portion of said electrical discharge which interacts with said laser radiation.

* * * * *